US005891844A

United States Patent [19]
Häfner

[11] Patent Number: 5,891,844
[45] Date of Patent: Apr. 6, 1999

[54] COMPOSITIONS FOR TREATING IRDS AND ARDS WITH A COMBINATION OF A GLUCOCORTICOSTEROID AND A LUNG SURFACTANT, AND THEIR USE

[75] Inventor: Dietrich Häfner, Constance, Germany

[73] Assignee: BYK Gulden Lomberg Chemische Fabrik GmbH, Constance, Germany

[21] Appl. No.: 809,687

[22] Filed: Jun. 19, 1997

[30] Foreign Application Priority Data

Sep. 28, 1994 [DE] Germany .......................... 443 46 29.8

[51] Int. Cl.⁶ .......................... A61K 38/16; A61K 31/56
[52] U.S. Cl. .................................. 514/7; 514/12; 514/171
[58] Field of Search ................... 514/7, 12, 171

[56] References Cited

U.S. PATENT DOCUMENTS 4,944,941  7/1990  Ammann ................................ 424/85.5

OTHER PUBLICATIONS

Medline 93175549, Jobe et al., *Am. J. Ostet. Gynecol.*, 168(2), 508–13 (1993 Feb.).
Medline 93326331, Robertson, *Ann. Med.*, 25(3), 285–8, Ref:23, (1993 Jun.).
Schrod et al., *Z. Geburtsh, Perinat.*, 197, 184–7 (1993).
Possmayer, Am Rev Respir Dis 138:990–998, 1988.
Kwong et al Pediatric Res. 21 (4.2) #1706, 1987.
Kari et al, Pediatrics pp. 730–736, Jan. 5, 1994.
Gladstone et al. J. Applied Physiol. 67(4) pp. 1377–1382, Oct. 1989.

*Primary Examiner*—Rebecca Cook
*Attorney, Agent, or Firm*—Jacobson, Price, Holman & Stern, PLLC

[57] ABSTRACT

Novel compositions for the treatment of IRDS and ARDS contain at least one glucocorticosteroid and a pulmonary surfactant. The duration of treatment with these compositions and the mortality associated with these syndromes can be significantly reduced with the administration of these compositions.

10 Claims, No Drawings

COMPOSITIONS FOR TREATING IRDS AND ARDS WITH A COMBINATION OF A GLUCOCORTICOSTEROID AND A LUNG SURFACTANT, AND THEIR USE

This is a 371 of PCT/EP95/03816 filed Sep. 27, 1998.

TECHNICAL FIELD

The invention relates to a novel composition for the treatment of IRDS and ARDS.

PRIOR ART

It is well known, that a treatment of pregnant women tending to premature birth with glucocorticosteroid (GCS) may mitigate the consequences of Infant Respiratory Distress Syndromes (=IRDS) for their babies (e. g. H. R. Gamsu, B. M. Mullinger, P. Donai and C. H. Dash: Antenatal administration of Betamethasone to prevent respiratory distress syndrome in preterm infants: report of a UK multicentre trial, Brit J. Obst. Gyn. 1989, 96:410-10; Review: A. N. Papageorgiou and L. Stern: J. Perinat Med. 1986, 14:75–486). For this reason the expectant mothers are treated with GCS. Then one tries to delay birth for at least 24 hours in order to attain the maturing effect of GCS on the lung. Since several years preterm infants arm treated with lung surfactants (LSF) by in intratracheal or intabronchial instillation in order to prevent and/or treat IRDS (A. Jobe and M. Ikegami: Surfactant for the treatment of respiratory distress syndrome, Am. Rev. Respir. Dis. 1987, 138:1256–75; M. S. Reynolds and K. A. Wallander. Use of surfactant in the prevention and therapy of neonatal respiratory distress syndrome, Clin. Pharm. 1969, 8:559–76). Since some time there are more and more pivotal studies where LSF is successfully used for the treatent of the Acute Respiratory Distress Syndrome (ARDS) of different formation. (Overview e.g. B. B. Lachmann, D. Gommers and E. P. Eijking: Exogenous surfactant therapy in adults, Atemw.-Lungenkrkh, 1993, 19:581–91; T. J. Gregory et al,; Survanta supplementation in patients wit acute respiratory distress syndrome (ARDS), Am. J. Respir. Crit. Care Med. 1994, 149:A567). Corticosteroids are applied for ARDS with only little success (G. R. Bernard et al.: High-dose corticosteroids in patients with the adult respiratory distress syndrome, N. Engl. J. Med. 1987, 317:1565–70).

DESCRIPTION OF THE INVENTION

It now was surprisingly found, that by the application of a combination of glucocorticosteroid and lung surfactants a synergistic effect in the treatment of IRDS and ARDS can be attained.

The Invention therefore relates to a composition for the treatment of IRDS and ARDS containing at least one glucocorticosteroid and a lung surfactant.

Further embodiments of the invention can be taken from the patent claims.

As gluoccorticosteroids those are or interest which are appropriate for the application in the lung. By way of example betamethasone, methylprednisolone, dexamethasone and ciclesonide are mentioned.

According to this invention under lung surfactants those of the numerous known compositions are to be understood which show the function of the natural lung surfactant. With these compositions preferably phospholipids are meant, which among others may additionally contain lung surfactant proteins. Of the commercial products are to be mentioned Curosurf® (Serono, Pharma GmbH, 85716 Unterschleißheim), which is a highly purified natural surfactant from homogenised pig lungs, Survanta® (Abbot GmbH, Wiesbaden) and Alveofact® (Dr. Karl Thomas GmbH Biberach), which both are extracts from cattle lungs, and Exosurf® (Deutsche Wellcome GmbH, Burgwedel), a synthetic phospholipid containing auxiliaries. As lung surfactants both proteins from natural sources like, for example, lung lavage or extraction from amniotic fluid as well as proteins produced by genetic engineering come into consideration. In connection with this invention preferably the lung surfactant proteins denominated SP-B and SP-C and their modified derivatives are of interest. The amino acid sequences of these lung surfactant proteins, their isolation or production by genetic engineering are known (WO86/03408, EP-A-0251449, WO89/04326, WO-87/06943, WO88/03170, EP-A-0368823 and EP-A-0348967). In EP-B0100910, EP-A-0110498, EP-B-0119056, EP-B0145005 and EP-B-0286011 compositions of phospholipids with and without lung surfactant proteins are described, which by way of example are of interest as components of the compositions according to this invention.

The compositions according to this invention are provided either as powder for the inhalative application or in fluid form for the intratracheal or intrabronchial application. A powder is obtained by lyophilising and micronising fluid lung surfactant preparations before or after the addition of glucocorticosteroids. Compositions according to this invention contain 1 to 30 weight percent of glucocorticosteroid (dependent from the efficacy of the GCS; a table with relative values of the efficacies of glucocorticosteroids can be taken from Goodman/Gillman, Pharmacological Basis of Therapeutics, Pergamon Press, page 1447, 8th Ed.) and 15 to 95 weight percent of lung surfactant of the dry mass (e. g. betamethasone 7% and LSF 92% or methylprednisolone 37% and LSF 63%)

The compositions according to this invention are applied 3 to 4 times daily for 2 to 4 days. As an example preparations containing 4 mg betamethasone and 50 mg phospholipids are applied 6 times every 8 hours by inhalation or intratracheally or intrabronchially.

Pharmacology

Adult Sprague Dawey rats are artificially ventilated with pure oxygen and a positive end-expiratory pressure (=PEEP; in order to guarantee the oxigenisation of the rats) and so often subjected to a lavage until their own LSF is washed out (B. Lachmann, B. Robertson and J. Vogel: In vivo lung-lavage as an experimental model of the respiratory distress syndrome, Acta Anesth. Scand. 1980, 24:231–6; D. Häfner, U. Kilian and R. Beume: Comparison of four lung surfactant preparations in an animal model of adult respiratory distress syndrome (ARDS). Am. Rev. Respir. Dis. 1993, 147;A719; D. Häfner, P. G, Germann, D. Hauschke, Pulmonary Pharmacology (1994)7, 319–332.). This is manifested by the fact that the animals' starting values of the arterial oxygen partial pressure (PaO2) of 500–550 mmHg (ventilation with pure oxygen and PEEP) drop down to values of 50–110 mmHg. Animals of the control group, which are not treated with LSF, continue to exhibit these low values of PaO2 during the examination period. Five minutes after the PaO2 dropped to these values, LSF or LSF together with a glucocorticosteroid, are instilled intratracheally. Blood gases are determined 5, 30, 60, 90 and 120 minutes after instillation. Then the PEEP is reduced from 8 to 6 cm $H_2O$ (first reduction of the PEEP). After further 15 minutes the PEEP is reduced to 3 cm $H_2O$ (second reduction of the PEEP). Blood gases are determined 5 minutes after both reductions of PEEP.

The following table 1 row A shows the mean values (±standard deviation) of the PaO2 in mmHg over the period of 5 to 120 minutes (constant PEEP of 8 cm $H_2O$) after the intratracheal instillation. Row B shows the mean values (±standard deviation) of the PaO2 after the first reduction of the PEEP after the intratracheal instillation. From row C the mean values (±standard deviation) of the PaO2 during the second reduction of the PEEP can be taken. The table shows that the sole application of glucocorticosteroid (in this case budesonide) does not influence the PaO2. This follows from the comparison with the untreated control animals. The application of LSF (25 or 100 mg/kg) brings about a rise of the PaO2. The addition of 600 μg budesonide to each dosage of LSF improves the values of PaO2 significantly in comparison to the respective dosages of LSF. From this follows that the combined application of glucocorteroids and LSF leads to an unexpected synergistic effect. Therefore it is possible either to save a portion of the very expensive LSF or to attain an enhanced effect of each of the components.

TABLE 1

|   | Control | Budesonide 600 μg/kg | LSF 25 mg/kg | LSF 25 mg/kg + Budesonide 600 μg/kg | LSF 100 mg/kg | LSF 100 mg/kg + Budesonide 600 μg/kg |
|---|---|---|---|---|---|---|
| A | 82 ± 30 | 61 ± 17 | 396 ± 49 | 453 ± 50 | 496 ± 35 | 525 ± 16 |
| B | 77 ± 23 | 96 | 316 ± 91 | 437 ± 71 | 461 ± 72 | 533 ± 25 |
| C | 50 ± 8 | 58 | 103 ± 63 | 251 ± 156 | 170 ± 127 | 341 ± 103 |

The histopathological examination of to lungs of these animals after the end of the experiment shows a severe formation of so-called hyaline membranes (HM) and a strong infiltration of inflammatory cells [a.g. polymorphonuclear neutrophil leukocytes (=PMNL)] as the symptom of the development of an acute respiratory distress syndrome.

The examination of preparations according to this invention containing dexamethasone or ciclesonide and a mixture of phospholipids showed oxygenation and histological changes (inhibition of the formation of HM and inhibition of the infiltration of PMNL) in comparison to the sole application of LSF or GCS are synergistically improved. From this follows that because of this unexpected synergistic effect the treatment of IRDS and ARDS can be shortened and the high morality in connection with these syndromes can be reduced.

I claim:

1. A composition for treating IRDS (Infant Respiratory Distress Syndrome) and ARDS (Acute Respiratory Distress Syndrome) comprising a synergistic combination of a glucocorticosteroid and a lung surfactant.

2. A composition according to claim 1, wherein the glucocorticosteroid is betamethasone, methylprednisolone, dexamethasone or ciclesonide.

3. A composition to claim 1, wherein the lung surfactant is a mixture of phospholipids.

4. A composition according to claim 3, wherein each phospholipid is one which is present in a natural lung surfactant.

5. A composition according to claim 3, which further comprises a lung surfactant protein.

6. A composition according to claim 5, which further comprises SP-B and/or SP-C and/or one or more modified derivatives thereof.

7. A composition according to claim 4, which further comprises a surfactant obtained by lung lavage.

8. A composition having an active component for treating IRDS and ARDS, the active component consisting essentially of glucocorticosteroid and lung surfactant.

9. A method of treating IRDS or ARDS which comprises administering an effective amount of a composition of claim 1 to a subject afflicted with one of these syndromes.

10. In a composition which is useful for treating IRDS (Infant Respiratory Distress Syndrome) or ARDS (Acute Respiratory Distress Syndrome) and which has an active component for that purpose, the improvement wherein the active component is a synergistic combination of pharmaceutically-active ingredients comprising a glucocorticosteroid and a lung surfactant.

* * * * *